(12) United States Patent
Eddins et al.

(10) Patent No.: US 12,177,631 B2
(45) Date of Patent: *Dec. 24, 2024

(54) DEVICE FOR TARGETED FEATURE-SPECIFIC SENSORY THERAPY

(71) Applicant: University of South Florida, Tampa, FL (US)

(72) Inventors: David Eddins, Odessa, FL (US); Joseph Walton, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/301,536

(22) Filed: Apr. 17, 2023

(65) Prior Publication Data

US 2023/0336927 A1 Oct. 19, 2023

Related U.S. Application Data

(63) Continuation of application No. 16/604,728, filed as application No. PCT/US2018/027676 on Apr. 13, 2018, now Pat. No. 11,632,633.

(60) Provisional application No. 62/485,194, filed on Apr. 13, 2017.

(51) Int. Cl.
*H04R 25/00* (2006.01)

(52) U.S. Cl.
CPC .......... *H04R 25/50* (2013.01); *H04R 25/604* (2013.01); *H04R 25/70* (2013.01); *H04R 2225/41* (2013.01)

(58) Field of Classification Search
CPC .. H04R 2225/41; H04R 25/50; H04R 25/604; H04R 25/70
USPC ............................................................ 600/28
See application file for complete search history.

(56) References Cited

U.S. PATENT DOCUMENTS

| | | |
|---|---|---|
| 5,645,074 A | 7/1997 | Shennib et al. |
| 5,813,862 A | 9/1998 | Merzenich et al. |
| 2002/0078750 A1 | 6/2002 | Wright et al. |
| 2006/0029912 A1 | 2/2006 | Kearby et al. |
| 2010/0046778 A1* | 2/2010 | Crawford ............. H04R 25/604 381/322 |

OTHER PUBLICATIONS

International Search Report and Written Opinion in PCT/EP2018/027676. Mailed Jul. 2, 2018. 6 pages.

* cited by examiner

*Primary Examiner* — Phylesha Dabney
(74) *Attorney, Agent, or Firm* — Meunier Carlin & Curfman LLC

(57) ABSTRACT

A device and method that supplements sensory input, thereby providing a supplemented sensory environment, to induce plasticity within the central nervous system that effectively overcomes sensory-neural processing deficits or strengthens specific sensory-neural abilities. In one implementation, ear-level hearing devices are used to deliver therapeutic sound with specific acoustic features that serve as archetypes of stimulus features for which sensory-neural processing is compromised by a sensory-neural deficit.

19 Claims, 2 Drawing Sheets

DEVICE FOR TARGETED FEATURE-SPECIFIC SENSORY THERAPY

CROSS-REFERENCE TO RELATED APPLICATION(S)

This application is a continuation of U.S. National Stage application Ser. No. 16/604,728, filed on Oct. 11, 2019, which is a National Stage of International Application No. PCT/US2018/027676, filed on Apr. 13, 2018, which claims priority to U.S. Provisional Patent Application No. 62/485,194, filed on Apr. 13, 2017, the entire disclosures of which are incorporated herein by reference.

STATEMENT REGARDING FEDERALLY SPONSORED RESEARCH OR DEVELOPMENT

This invention was made with government support AG009524 and DC015054 awarded by the National Institutes of Health. The Government has certain rights to the invention.

BACKGROUND OF THE INVENTION

Normal and effective sensory processing involves the extraction, encoding, and weighting of stimulus input in a manner that provides an internal neural representation of stimulus features, patterns, or changes in those features and patterns. Sensory deficits lead to weak or altered internal neural representation of stimulus features, patterns, or changes in those features and patterns.

Early childhood sensorineural hearing loss (SNHL) is a common neurosensory disability causing significant medical, social and financial hardship. The prevalence of moderate-to-profound SNHL in children (>40 dB) is roughly 3 in 1,000 with up to 10% have hearing loss considered "profound". There are numerous causes of congenital or acquired sensorineural hearing loss including genetic factors, environmental infections or toxins and unknown causes. Beyond the threshold deficits seen in children with SNHL, studies have also shown functional difficulty with development of normal speech and language processing. Importantly, deficits in fundamental perceptual attributes involving temporal processing have been associated with impairments in speech perception.

SUMMARY OF THE INVENTION

Previous studies have shown that early exposure to a simple augmented acoustic environment (AAE) can limit the effects of progressive hearing loss by rescuing peripheral function, presumably though a reduction in outer hair cell (OHC) death. Only a few studies have investigated the effects of more complex AAE. These studies built upon the information above showing that changes during development affect the central auditory system.

The technology described herein overcomes such sensory deficits by chronically supplementing the sensory experience with perceptually salient but unobtrusive stimuli that have stimulus features that target the specific sensory deficit to be treated.

Accordingly, embodiments of the invention provide an ear-level hearing device to support active sound therapy using specific therapeutic sounds that target specific sensory deficits and effectively overcomes those deficits by altering the way in which the central nervous system encodes, processes, or weights incoming sensory information.

One unique approach with embodiments of the invention is that the invention uses targeted therapeutics such that the treatment is designed to target specific sensory deficits through the use of archetypal stimuli that coincide with said deficits.

In one embodiment, the invention provides a system for targeted feature-specific sensory therapy. The system comprises a hearing device configured to provide an augmented acoustic environment, determine an archetypal stimuli associated with a specific sensory deficit, and supplement the augmented acoustic environment with the archetypal stimuli.

In another embodiment, the invention provides a method of targeted feature-specific sensory therapy. The method comprises providing, with a hearing device, an augmented acoustic environment; determining a peripheral function; monitoring neural response properties following augmented acoustic environment exposure via the hearing device; determining whether a patterned temporal augmented acoustic environment stimulus improves neural correlates of temporal processing; and when the patterned temporal augmented acoustic environment stimulus improves neural correlates of temporal processing, supplementing the augmented acoustic environment with the patterned temporal augmented acoustic environment stimulus.

In one construction, the monitoring of the neural response properties includes monitoring at least one selected from a group consisting of tuning sharpness, frequency representation, excitatory drive, and temporal acuity.

In another construction, the determining of the peripheral function includes determining the peripheral function using auditory brainstem response thresholds and functional outer hair cell assessment.

In yet another construction, the determining whether a patterned temporal augmented acoustic environment stimulus improves neural correlates of temporal processing includes determining whether passive exposure to the patterned temporal augmented acoustic environment stimulus improves neural correlates of gap detection.

Other aspects of the invention will become apparent by consideration of the detailed description and accompanying drawings.

DETAILED DESCRIPTION

Figure 1A:
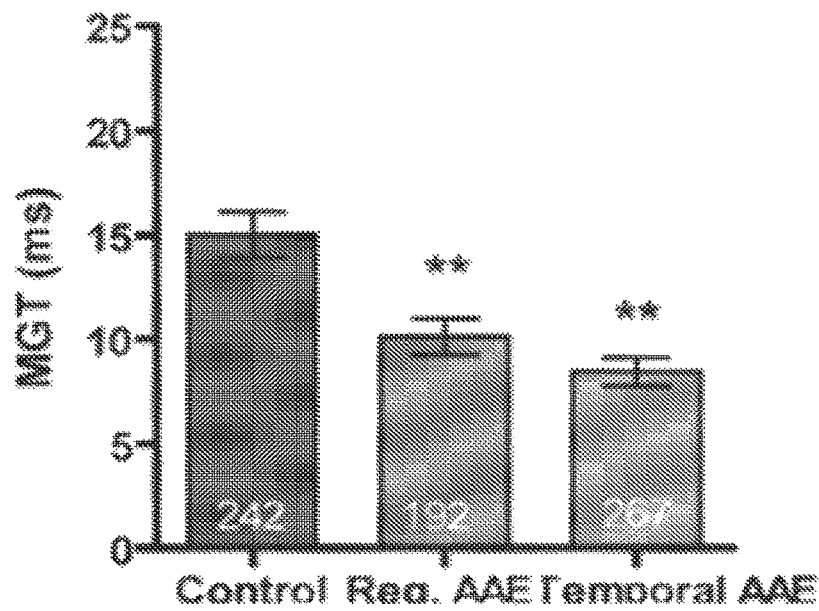
FIG. 1A is a graph illustrating neural correlates of gap detection where the 80-dB carrier level exposure to both types of AAE resulted in shorter mean MGT.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The invention according to some embodiments involves technology that chronically supplements sensory input, thereby providing a supplemented sensory environment, to induce plasticity within the central nervous system that effectively overcomes sensory-neural processing deficits or strengthens specific sensory-neural abilities. In one implementation of this technology, an ear-level hearing device is used to deliver therapeutic sound with specific acoustic features that serve as archetypes of stimulus features for which sensory-neural processing is compromised by a sensory-neural deficit. Use cases include but are not limited to the following:

(1) Given a sensory processing deficit that leads to impaired temporal envelope processing, the therapeutic technology involves generation of a sound with a range of relevant temporal envelope features and chronic delivery of this sound through the ear-level device at a presentation level that renders the features audible and relevant but not bothersome or interfering with normal everyday tasks.

(2) Given a sensory processing deficit that leads to an impaired ability to separate sounds of interest from competing sounds, the therapeutic technology involves generation of a sound with a range of relevant target-background combinations and chronic delivery of this sound through the ear-level device at a presentation level that renders the features audible and relevant but not bothersome or interfering with normal everyday tasks.

(3) Given a sensory processing deficit that leads to impaired perception of fine temporal details, the therapeutic technology involves generation of a sound with a range of relevant rapid temporal patterns and chronic delivery of this sound through the ear-level device at a presentation level that renders the features audible and relevant but not bothersome or interfering with normal everyday tasks.

(4) Given a sensory processing deficit that leads to an impaired ability to use binaural difference cues, the therapeutic technology involves generation of a sound with a range of relevant interaural differences and chronic delivery of this sound through the ear-level device at a presentation level that renders the features audible and relevant but not bothersome or interfering with normal everyday tasks.

(5) Given a sensory processing deficit that leads to an impaired ability to use spectral features, the therapeutic technology involves generation of a sound with a range of relevant spectral features and chronic delivery of this sound through the ear-level device at a presentation level that renders the features audible and relevant but not bothersome or interfering with normal everyday tasks.

(6) Given a sensory processing deficit that leads to an impaired ability to encode stimulus loudness, the therapeutic technology involves generation of a sound with a range of relevant intensive features and chronic delivery of this sound through the ear-level device at a presentation level that renders the features audible and relevant but not bothersome or interfering with normal everyday tasks.

Figure 2:
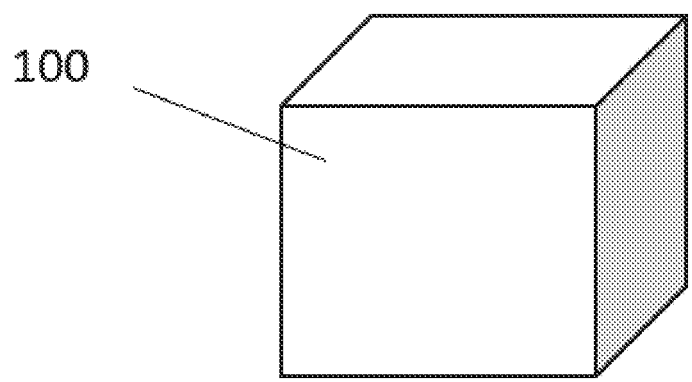
FIG. 2 is a schematic representation of an example hearing device.

FIG. 2 is a schematic representation of an example hearing device 100. The ear-level hearing device 100, according to an embodiment of the invention, may be earphones, headsets, hearing aids, cochlear implants, or the like. In one construction, the ear-level hearing device 100 generates the sounds and delivers the sounds to the user. In another construction, the sound is output to a user (e.g., at 70 dB Sound Pressure Level (SPL)) from a speaker that may be positioned on a support (e.g., speaker stand, table, platform, or the like). In a further construction, the sound is output to a user via direct connection (e.g., cable, cord, link, or the like) or wirelessly via a network (e.g., Wi-Fi, Bluetooth, or the like).

Psychoacousticians have used gap detection paradigms to evaluate temporal acuity for more than 30 years. Minimal gap threshold (MGT) correlates well to voice onset time (VOT), the interval between consonant release and the start of vocal cord vibration in consonant-vowel transitions. Temporal processing ability during child development and in adults has been linked to speech recognition abilities and normal language development. Furthermore, gap detection can also be measured in animal models using several different behavioral techniques and results indicate that nearly all mammals have similar MGTs, which are on the order of 2-3 msec. In addition, neural correlates of gap detection have been shown to approximate behavioral measures in single-neuron recordings from inferior colliculus (IC) neurons of young mice.

There are several mouse models that mimic several of the different types and progressive nature of congenital SNHL. The DBA strain, the oldest inbred mouse strain contains a mutation to the gene Cdh23, as well as a nucleotide substitution in the fascin-2 gene (Fscn2), the causative gene of the Ah18 modifier locus. This strain shows a rapid, progressive loss in peripheral function beginning at the onset of hearing and display many of the audiometric characteristics found in infants with progressive sensorineural hearing loss. DBA mice have early and rapid loss of OHC function in a base to apex progression, as measured by distortion product otoacoustic emission (DPOAE) thresholds.

Previous studies have shown that when newborn DBA mice are exposed to broadband sounds, on a daily basis, over 12-hour cycles results in improved peripheral and central auditory function. In addition to preserving hearing sensitivity, exposure to this augmented acoustic environment (AAE) limits hair cell loss. In the central auditory system, AAE exposure preserves AVCN volume and neuronal cell counts, possibly by maintaining afferent neuronal input to the auditory brainstem. Additionally, AAE exposure expands the frequency range that IC neurons are sensitive to across the dorso-ventral axis compared to non-exposed mice. When normal-hearing, young adult CBA mice are exposed to AAE no effects, positive or negative, are observed (Willott, Turner, & Sundin, 2000). Clearly, in mouse models of congenital SNLH, AAE exposure shows promise in ameliorating the effects of rapid progressive SNHL, but its usefulness in other auditory domains has yet to be studied.

Figure 1B:
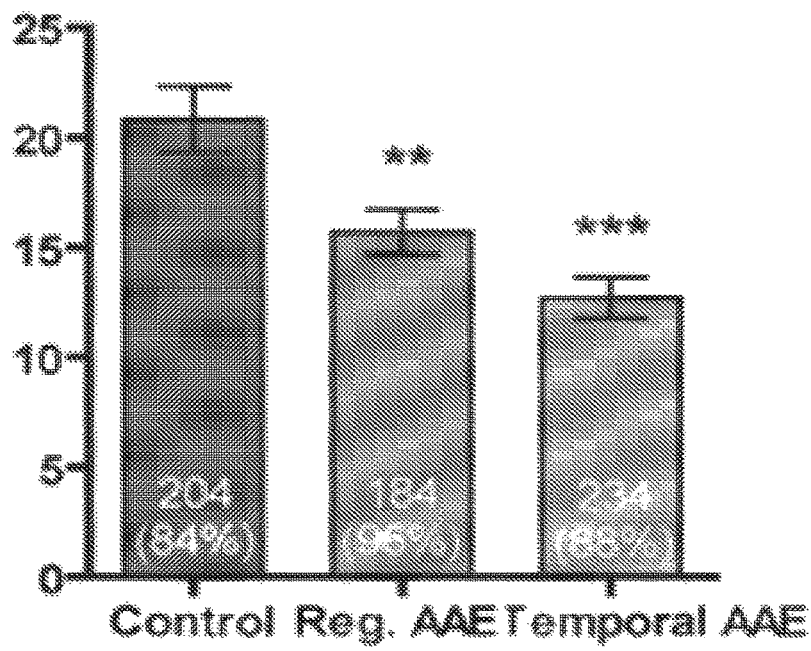
FIG. 1B is a graph illustrating neural correlates of gap detection where the 70-dB carrier level exposure to both types of AAE again shorten mean MGT, with greater improvement seen in the temporal AAE exposure group.

Gap detection improved in phasic units following exposure to both types of AAE, with greater improvement seen following exposure to a novel temporal AAE. Representative post-stimulus time histograms (PSTHs) from a single unit in each exposure group, at different gap durations, are shown in FIGS. 1A and 1B. Mean gap thresholds (MGTs) were computed across all responding units in each exposure group, where responding units are units with a gap threshold ≤96 ms. At the 80-dB carrier level (FIG. 1A), both types of AAE shorten mean MGT (one-way ANOVA, $F=15.43$, $p<0.001$). The magnitude of the improvement between regular AAE exposure and control was 4.89 ms (a 33% improvement), and between temporal AAE exposure and control was 6.58 ms (a 44% improvement). At the 70-dB carrier level (FIG. 1B), both types of AAE exposure also improve the mean MGT compared to controls ($F=12.49$, $p<0.001$), with greater improvement seen by mice exposed to temporal AAE ($12.7\pm1.0$ ms versus $20.8\pm1.5$ ms, $p<0.001$). At all levels, temporal AAE-exposed mice had the greatest percent of phasic units with the shortest gap thresholds. The impact of AAE on the response to gaps by tonic units was minimal and showed no significant effects of AAE exposure on gap thresholds (data not shown).

Exposure to temporal AAE also preserved neural correlates of gap detection in the presence of continuous background noise (CBN). Only a subset of phasic units were responsive in background noise. In the presence of +6 dB SNR continuous background noise (an 80-dB SPL carrier presented with 74-dB SPL CBN) a significant effect of exposure on MGT was observed (one-way ANOVA: F=5.39, p=0.005). Exposure to temporal AAE significantly shortened MGTs compared to controls (12.7±1.0 ms versus 17.9±1.2 ms, p<0.01) while exposure to regular AAE trended towards shorter MGTs (14.6±1.2 ms versus 17.9±1.2 ms, p>0.05). Tonic units recorded in continuous background noise demonstrated post-excitatory suppression. Due to post-excitatory suppression, the quiet window responses of these units were not strictly a result of the embedded silent gap making gap detection threshold determination highly variable. This increased variability for tonic responders prevented reliable determination of the MGT.

As illustrated in FIGS. 1A and 1B, neural correlates of gap detection are improved following 60 days of patterned AAE exposure. Exposure to both types of AAE (regular and temporal) improve mean gap thresholds in phasic units. Mean gap thresholds (MGTs) were computed across each group, for each noise carrier level (80, 70 & 60 dB). As seen in FIG. 1A, the 80-dB carrier level exposure to both types of AAE resulted in shorter mean MGT (Control: 15.0±1.1 ms, Reg. AAE: 10.1±0.9, Temporal AAE: 8.4±0.7 ms). As seen in FIG. 1B, the 70-dB carrier level, exposure to both types of AAE again shorten mean MGT, with greater improvement seen in the temporal AAE exposure group (Control: 20.8±1.5 ms, Reg. AAE: 15.7±1.0, Temporal AAE: 12.7±1.0 ms).

Various features and advantages of the invention are set forth in the following claims.

What is claimed is:

1. A method of providing targeted feature-specific sensory therapy comprising:
    providing, with a hearing device, an augmented acoustic environment,
    determining an archetypal stimuli associated with a specific sensory deficit, and
    supplementing the augmented acoustic environment with the archetypal stimuli,
    wherein, when the specific sensory deficit includes impaired perception of fine temporal details, supplementing the augmented acoustic environment with the archetypal stimuli includes generating a sound with a range of relevant rapid temporal patterns and chronically delivering the sound at a presentation level that renders the features audible and relevant,
    wherein when the specific sensory deficit includes impaired temporal envelop processing, supplementing the augmented acoustic environment with the archetypal stimuli includes generating a sound with a range of relevant temporal envelope features and chronically delivering the sound at a presentation level that renders the features audible and relevant.

2. The method of claim 1, wherein when the specific sensory deficit includes impaired ability to separate sounds of interest from competing sounds, supplementing the augmented acoustic environment with the archetypal stimuli includes generating a sound with a range of relevant target-background combinations and chronically delivering the sound at a presentation level that renders the features audible and relevant.

3. The method of claim 1, wherein when the specific sensory deficit includes impaired ability to use binaural difference cues, supplementing the augmented acoustic environment with the archetypal stimuli includes generating a sound with a range of relevant interaural differences and chronically delivering the sound at a presentation level that renders the features audible and relevant.

4. The method of claim 1, wherein the archetypal stimuli is designed to target the specific sensory deficit.

5. The method of claim 1, wherein the specific sensory deficit includes impaired ability to use spectral features.

6. The method of claim 5, wherein supplementing the augmented acoustic environment with the archetypal stimuli includes generating a sound with a range of relevant spectral features and chronically delivering the sound at a presentation level that renders the features audible and relevant.

7. The method of claim 1, wherein the specific sensory deficit includes impaired ability to encode stimulus loudness.

8. The method of claim 7, wherein supplementing the augmented acoustic environment with the archetypal stimuli includes generating a sound with a range of relevant intensive features and chronically delivering the sound at a presentation level that renders the features audible and relevant.

9. A method of providing targeted feature-specific sensory therapy:
    providing, with a hearing device, an augmented acoustic environment,
    determining an archetypal stimuli associated with a specific sensory deficit, and
    supplementing the augmented acoustic environment with the archetypal stimuli,
    wherein the specific sensory deficit includes impaired ability to use binaural difference cues.

10. The method of claim 9, wherein supplementing the augmented acoustic environment with the archetypal stimuli includes generating a sound with a range of relevant interaural differences and chronically delivering the sound at a presentation level that renders the features audible and relevant.

11. The method of claim 9, wherein the wherein the specific sensory deficit includes at least one of: impaired temporal envelop processing; impaired ability to separate sounds of interest from competing sounds; impaired perception of fine temporal details; impaired ability to use spectral features; or impaired ability to encode stimulus loudness;
    wherein, when the specific sensory deficit includes temporal envelop processing, supplementing the augmented acoustic environment with the archetypal stimuli includes generating a sound with a range of relevant temporal envelope features and chronically delivering the sound at a presentation level that renders the features audible and relevant,
    wherein, when the specific sensory deficit includes impaired ability to separate sounds of interest from competing sounds, supplementing the augmented acoustic environment with the archetypal stimuli includes generating a sound with a range of relevant target-background combinations and chronically delivering the sound at a presentation level that renders the features audible and relevant,
    wherein, when the specific sensory deficit includes impaired perception of fine temporal details, supplementing the augmented acoustic environment with the archetypal stimuli includes generating a sound with a range of relevant rapid temporal patterns and chronically delivering the sound at a presentation level that renders the features audible and relevant, wherein, when the specific sensory deficit includes impaired ability to use spectral features, supplementing the augmented acoustic environment with the archetypal stimuli includes generating a sound with a range of relevant spectral features and chronically delivering the sound at a presentation level that renders the features audible and relevant, wherein, when the specific sensory deficit includes impaired ability to encode stimulus loudness, supplementing the augmented acoustic environment with the archetypal stimuli includes generating a sound with a range of relevant intensive features and chronically delivering the sound at a presentation level that renders the features audible and relevant.

12. A method of providing targeted feature-specific sensory therapy comprising:
providing, with a hearing device, an augmented acoustic environment,
determining an archetypal stimuli associated with a specific sensory deficit, and
supplementing the augmented acoustic environment with the archetypal stimuli,
wherein the specific sensory deficit includes impaired ability to use spectral features,
wherein the specific sensory deficit includes at least one of: impaired temporal envelop processing; impaired ability to separate sounds of interest from competing sounds; impaired perception of fine temporal details; impaired ability to use binaural difference cues; or impaired ability to encode stimulus loudness,
wherein, when the specific sensory deficit includes impaired ability to use binaural difference cues, supplementing the augmented acoustic environment with the archetypal stimuli includes generating a sound with a range of relevant interaural differences and chronically delivering the sound at a presentation level that renders the features audible and relevant.

13. The method of claim 12, wherein supplementing the augmented acoustic environment with the archetypal stimuli includes generating a sound with a range of relevant spectral features and chronically delivering the sound at a presentation level that renders the features audible and relevant.

14. The method of claim 12,
wherein, when the specific sensory deficit includes temporal envelop processing, supplementing the augmented acoustic environment with the archetypal stimuli includes generating a sound with a range of relevant temporal envelope features and chronically delivering the sound at a presentation level that renders the features audible and relevant,
wherein, when the specific sensory deficit includes impaired ability to separate sounds of interest from competing sounds, supplementing the augmented acoustic environment with the archetypal stimuli includes generating a sound with a range of relevant target-background combinations and chronically delivering the sound at a presentation level that renders the features audible and relevant,
wherein, when the specific sensory deficit includes impaired perception of fine temporal details, supplementing the augmented acoustic environment with the archetypal stimuli includes generating a sound with a range of relevant rapid temporal patterns and chronically delivering the sound at a presentation level that renders the features audible and relevant,
wherein, when the specific sensory deficit includes impaired ability to encode stimulus loudness, supplementing the augmented acoustic environment with the archetypal stimuli includes generating a sound with a range of relevant intensive features and chronically delivering the sound at a presentation level that renders the features audible and relevant.

15. A method of providing targeted feature-specific sensory therapy comprising:
providing, with a hearing device, an augmented acoustic environment;
determining a peripheral function;
monitoring neural response properties following augmented acoustic environment exposure via the hearing device;
determining whether a patterned temporal augmented acoustic environment stimulus improves neural correlates of temporal processing; and
when the patterned temporal augmented acoustic environment stimulus improves neural correlates of temporal processing, supplementing the augmented acoustic environment with the patterned temporal augmented acoustic environment stimulus.

16. The method of claim 15, wherein monitoring of the neural response properties includes monitoring at least one of tuning sharpness, frequency representation, excitatory drive, or temporal acuity.

17. The method of claim 15 further comprising:
monitoring the peripheral function; and
determining whether the patterned temporal augmented acoustic environment stimulus improves the monitored peripheral function.

18. The method of claim 15, wherein determining of the peripheral function includes determining the peripheral function using at least one of auditory brainstem response thresholds or functional outer hair cell assessment.

19. The method of claim 15, wherein determining whether the patterned temporal augmented acoustic environment stimulus improves neural correlates of temporal processing includes determining whether passive exposure to the patterned temporal augmented acoustic environment stimulus improves neural correlates of gap detection.

* * * * *